United States Patent [19]
Tomiyama et al.

[11] Patent Number: 5,409,947
[45] Date of Patent: Apr. 25, 1995

[54] CYCLOHEPTIMIDAZOLE DERIVATIVES, METHOD OF MANUFACTURING THE SAME AND THERAPEUTIC AGENTS CONTAINING THESE COMPOUNDS

[75] Inventors: Tsuyoshi Tomiyama; Akira Tomiyama, both of Nagano; Takashi Yanagisawa, Kousyoku; Naoto Ueyama, Ueda; Tomoyuki Kawai; Motoharu Sonegawa, both of Nagano; Hiromi Baba, Ueda; Makoto Haketa, Nagano, all of Japan

[73] Assignee: Kotobuki Seiyaku Co., Ltd., Nagano, Japan

[21] Appl. No.: 64,446

[22] Filed: May 21, 1993

[30] Foreign Application Priority Data

May 22, 1992 [JP]  Japan .................. 4-131142

[51] Int. Cl.⁶ .................. A61K 31/41; A61K 31/415; C07D 235/02; C07D 257/04
[52] U.S. Cl. .................. 514/381; 514/393; 548/250; 548/252; 548/253; 548/254; 548/302.7
[58] Field of Search .................. 548/302.7, 250, 252, 548/253, 254; 514/393, 381

[56] References Cited

U.S. PATENT DOCUMENTS

| | | | |
|---|---|---|---|
| 5,104,891 | 4/1992 | Bovy et al. | 548/302.7 |
| 5,250,554 | 10/1993 | Naka et al. | 548/252 |
| 5,281,615 | 1/1994 | Bovy et al. | 548/302.7 |

FOREIGN PATENT DOCUMENTS

0432737A1  11/1990  European Pat. Off. ......... 548/302.7

OTHER PUBLICATIONS

Med Chem Res. (1991) 1:86–94 Birkhauser Boston 1991, New Cycloheptimidazolones . . . Receptors, Bovy et al.
CA 115(21): 232241a Preparation . . . cardiovascular agents. Bovy et al., p. 950, 1991.
CA 116(23): 227646c New . . . receptors. Bovy et al., p. 19, 1992.

Primary Examiner—Mary C. Lee
Assistant Examiner—Joseph K. McKane
Attorney, Agent, or Firm—Sherman and Shalloway

[57]  ABSTRACT

New therapeutic agents of cycloheptimidazole derivatives are disclosed, which are represented by the following formula or its alkali-addition salts.

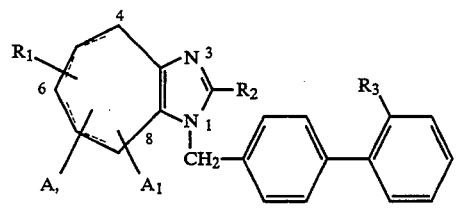

(wherein $R_1$ represents H or isopropyl group; $R_2$ represents a lower alkyl; $R_3$ represents a carboxylic acid or tetrazole group. A and $A_1$ are substituted groups at 4 or 8 position and $A_1$ is a hydrogen or hydroxy group when A is a hydrogen or A and $A_1$ is an oxo group. The dotted line "- - - -" is two double bonds or saturated single bonds).

These compounds are useful as anti-hypertensive or anti-congestive heart failure agents.

20 Claims, No Drawings

CYCLOHEPTIMIDAZOLE DERIVATIVES, METHOD OF MANUFACTURING THE SAME AND THERAPEUTIC AGENTS CONTAINING THESE COMPOUNDS

BACKGROUND OF THE INVENTION

1. Field of the Invention

This invention relates to a novel cycloheptimidazole derivative, a production method thereof, and a treatment agent for hypertension, congestive heart failure and intraocular pressure sthenia containing the cycloheptoimidazoles.

2. Description of the Prior Art

Many therapeutic agents have been developed as antihypertensive, anticongestive heart failure agents and intraocular pressure lowering agents. One approach is to use angiotensin converting enzyme (ACE) inhibitors. In the renin-angiotensine system (RAS), angiotensinogen is hydrolyzed to angiotensin I (AI) by the renin, and AI is converted to the final product, angiotensin II (AII), which has a strong vasoconstrictive action. It has been well known that AII is related to cause hypertension and congestive heart failure. These ACE inhibitors are currently used to inhibit the formation of AII. Another approach is to block the action of AII at the AII receptor level and several peptide-AII receptor antagonists are reported. However these AII receptor antagonists have a poor oral activity. From this reason, nonpeptide receptor antagonist having good oral activity has been required. Recently, several types of non-peptide compounds are proposed as angiotensin II receptor antagonists. For example, Japanese Patent Publications 1-117876 and 3-2169 describe imidazole derivatives, and Japanese Patent Publications 3-5480 and 3-5464 describe imidazopyridine derivatives.

3. Problem to be Solved by the Invention

A primary object of the present invention is to find a new cycloheptoimidazole derivative having an angiotensin II receptor antagonist effect and provide a treatment agent for hypertension and congestive heart failure or an intraocular pressure reducing agent and a production method thereof.

SUMMARY OF THE INVENTION

The principal object of the present invention is the provision of compounds having Angiotensin II receptor antagonistic activities.

Another object of the present invention is the provision of pharmaceutical compositions useful as antihypertensive agents.

Still another objects of the present invention is the provision of new cycloheptimidazole derivatives and a method for the manufacture there of.

These and other objects of the invention will become apparent from the description that follows.

DETAILED DESCRIPTION OF THE INVENTION

The inventors have conducted intensive studies on compounds having angiotensin II receptor antagonist effects, and found that there are compounds in cycloheptimidazole derivatives which have angiotensin II receptor antagonist effects in addition to the prior art imidazole derivatives or imidazopyridine derivatives, achieving the present invention.

In accordance with the present invention, there is provided a new cycloheptoimidazole derivative compound of Formula (1) or its salt capable of being used for medical treatment and a production method thereof.

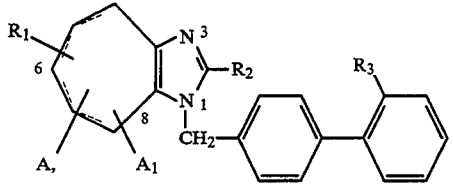

(wherein $R_1$ is hydrogen or isopropyl; $R_2$ represents a lower alkyl; $R_3$ represents a carboxyl or tetrazolyl; A and $A_1$ are individually substituents at 4- or 8-position, and $A_1$ is a hydrogen or hydroxy when A is a hydrogen or A and $A_1$ may form an oxo group; Line - - - - denotes two double bonds or saturated single bonds)

The compounds related to the general formula (1) possess a potent angiotensin II receptor antagonist and they are regarded as therapeutically useful.

The compounds related to the general formula (1) are exemplified as follows.

1. 5-[2-(4-(2-Methyl-8-oxo-1(8H)-cycloheptimidazolyl)-methylbiphenylyl)]tetrazole (Compound 1)
2. 5-[2-(4-(2-Ethyl-8-oxo-1(8H)-cycloheptimidazolyl)-methylbiphenylyl)]tetrazole (Compound 2)
3. 5-[2-(4-(2-Propyl-8-oxo-1(8H)-cycloheptimidazolyl)-methylbiphenylyl)]tetrazole (Compound 3)
4. 5-[2-(4-(2-Butyl-8-oxo-1(8H )-cycloheptimidazolyl)-methylbiphenylyl)]tetrazole (Compound 4)
5. 5-[2-(4-(2-Pentyl-8-oxo-1(8H)-cycloheptimidazolyl)-methylbiphenylyl)]tetrazole (Compound 5)
6. 4-(2-Butyl-8-oxo-1(8H)-cycloheptimidazolyl)methyl-biphenylyl-2-carboxylic acid (Compound 6)
7. 5-[2-(4-(2-Butyl-5-isopropyl-8-oxo-1(8H)-cycloheptimidazolyl)methylbiphenylyl)]tetrazole (Compound 7)
8. 5-[2-(4-(2-Butyl-6-isopropyl-8-oxo-1(8H)-cycloheptimidazolyl)methylbiphenylyl)]tetrazole (Compound 8)
9. 5-[2-(4-(2-Isopropyl-8-oxo-1(8H)-cycloheptimidazolyl)methylbiphenylyl)]tetrazole (Compound 9)
10. 5-[2-(4-(2-Isobutyl-8-oxo-1(8H)-cycloheptimidazolyl)methylbiphenylyl)]tetrazole (Compound 10)
11. 5-[2-(4-(2-Butyl-1, 4, 5, 6, 7, 8-hexahydro-1-cycloheptimidazolyl)methylbiphenylyl)]tetrazole (Compound 11)
12. 5-[2-(4-(2-Butyl-6-isopropyl-1, 4, 5, 6, 7, 8-hexahydro-1-cycloheptimidazolyl) methylbiphenylyl)]tetrazole (Compound 12)
13. 5-[2-(4-(2-Butyl-5-isopropyl-1, 4, 5, 6, 7, 8-hexahydro-1-cycloheptimidazolyl) methylbiphenylyl)]tetrazole (Compound 13)
14. 5-[2-(4-(2-Butyl-7-isopropyl-1, 4, 5, 6, 7, 8-hexahydro-1-cycloheptimidazolyl) methylbiphenylyl)]tetrazole (Compound 14)
15. 5-[2-(4-(2-Methyl-8-oxo-5, 6, 7, 8-tetrahydro-1-cycloheptimidazolyl)methylbiphenylyl)]tetrazole (Compound 15)
16. 5-[2-(4-(2-Ethyl-8-oxo-5, 6, 7, 8-tetrahydro-1-cycloheptimidazolyl)methylbiphenylyl)]tetrazole (Compound 16)

17. 5-[2-(4-(2-Propyl-8-oxo-5, 6, 7, 8-tetrahydro-1-cycloheptimidazolyl)methylbiphenylyl)]tetrazole (Compound 17)
18. 5-[2-(4-(2-Butyl-8-oxo-5, 6, 7, 8-tetrahydro-1-cycloheptimidazolyl)methylbiphenylyl)]tetrazole (Compound 18)
19. 5-[2-(4-(2-Pentyl-8-oxo-5, 6, 7, 8-tetrahydro-1-cycloheptimidazolyl)methylbiphenylyl)]tetrazole (Compound 19)
20. 5-[2-(4-(2-Butyl-4-oxo-5, 6, 7, 8-tetrahydro-1-cycloheptimidazolyl)methylbiphenylyl)]tetrazole (Compound 20)
21. 5-[2-(4-(2-Butyl-5-isopropyl-8-oxo-5, 6, 7, 8-tetrahydro-1-cycloheptimidazolyl) methylbiphenylyl)]tetrazole (Compound 21)
22. 5-[2-(4-(2-Butyl-6-isopropyl-8-oxo-5, 6, 7, 8-tetrahydro-1-cycloheptimidazolyl) methylbiphenylyl)]tetrazole (Compound 22)
23. 4-(2-Butyl-8-oxo-5, 6, 7, 8-tetrahydro-1-cycloheptimidazolyl)methylbiphenylyl-2-carboxylic acid (Compound 23)
24. 5-[2-(4-(Isopropyl-8-oxo-5, 6, 7, 8-tetrahydro-1-cycloheptimidazolyl)methylbiphenylyl)] tetrazole (Compound 24)
25. 5-[2-(4-(Isobutyl-8-oxo-5, 6, 7, 8-tetrahydro-1-cycloheptimidazolyl)methylbiphenylyl)]tetrazole (Compound 25)
26. 5-[2-(4-(2-Butyl-8-hydroxy-1, 4, 5, 6, 7, 8-hexahydro-1-cycloheptimidazolyl) methylbiphenylyl)]tetrazole (Compound 26)
27. 5-[2-(4-(2-Butyl-4-hydroxy-1, 4, 5, 6, 7, 8-hexahydro-1-cycloheptimidazolyl) methylbiphenylyl)]tetrazole (Compound 27)

The above-mentioned compounds numbered from 1 to 27 will be referred to hereinafter, as compound 1, compound 2, . . . compound 27 respectively.

The compound of general formula (1) can be obtained from the general formula (4) prepared from the reaction of the compound shown by the general formula (2) with a compound of the general formula (3).

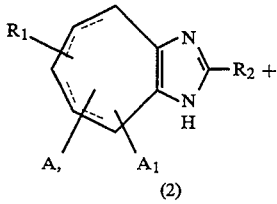

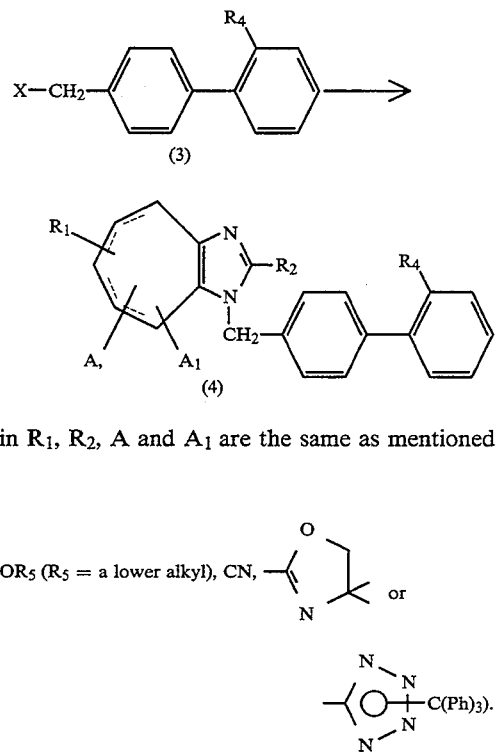

(wherein $R_1$, $R_2$, A and $A_1$ are the same as mentioned above;

$R_4$ is $COOR_5$ ($R_5$ = a lower alkyl), CN,

The reaction of cycloheptimidazole (2) and halogenomethyl biphenyl compound (3) can be generally carried out in the presence of a base. A base is used in this reaction such as sodium hydride, sodium hydroxide and potassium carbonate. As a solvent used in this reaction, dimethyl formamide (DMF), dimethyl sulfoxide (DMSO), tetrahydrofuran (THF), acetone and dioxane may be employed. Furthermore a phase transfer catalyst such as tetrabutyl ammonium hydrogen sulfate is applicable in this reaction and $H_2O$ and benzene are used as a solvent.

In case of A and $A_1$ is an oxo group and having two double bond in the compound of general formula (4a, b), these are prepared by the following reactions.

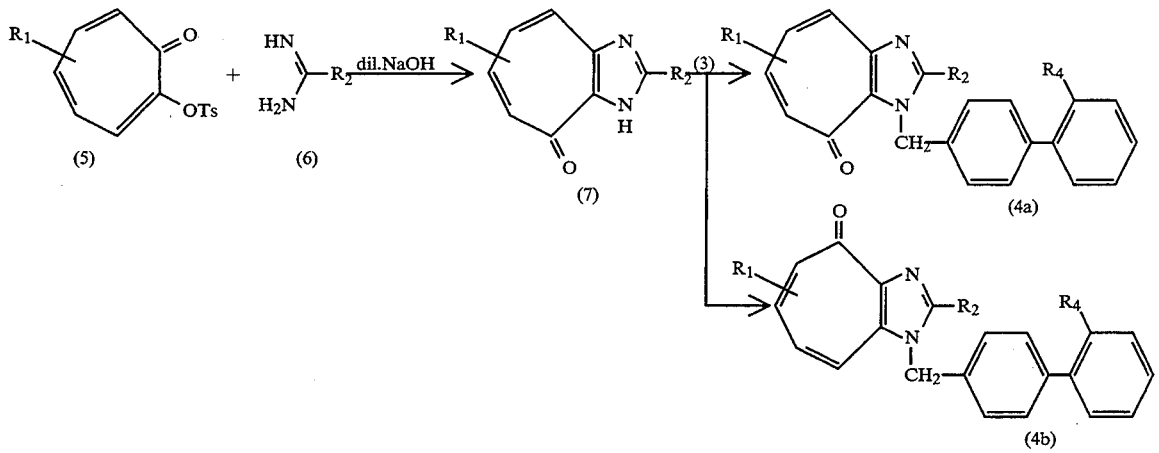

(wherein $R_1$, $R_2$ and $R_4$ are the same as mentioned above; Ts is a tosyl group.)

Tosyl tropolone (5) is reacted with amidine (6) in the presence of base to yield ketoimidazole (7) (C. A. 74, 53785a, J. Pat. 7031,171), and resulting ketoimidazole (7) is reacted with halogenomethyl biphenyl compound (3) to give the mixture of (4a) and (4b), which are chromatographically separated.

In case of A and $A_1$ are hydrogens and having the single bonds in the compound of general formula (4c), it is prepared by the following reactions.

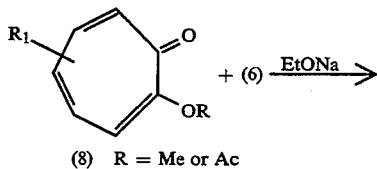

(8)   R = Me or Ac

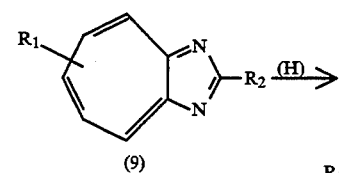

(9)

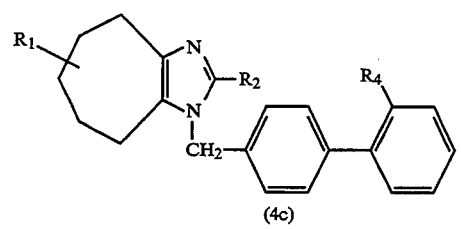

(4c)

(wherein $R_1$, $R_2$ and $R_4$ are the same as mentioned above.)

Methyl tropolone (8) is reacted with amidine (6) to give cycloheptimidazole (9), and (9) is hydrogenated over $PtO_2$ et cetera to yield 1, 4, 5, 6, 7, 8-hexahydrocycloheptimidazole (10), followed to react with the compound (3) to yield the compound (4c). In this reaction, $R_1$ being a lower alkyl, the regioisomer is obtained. The compound (4c) is purified by the usual manner.

In the case where A and $A_1$ form is an oxo group and have single bonds in the compounds of general formula (4d), it is prepared by the following reactions.

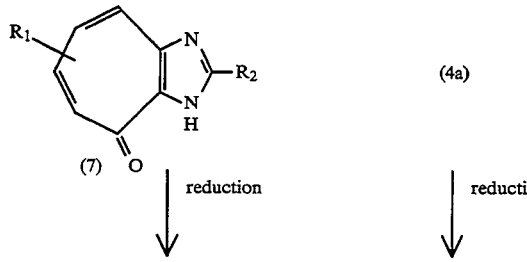

(4a)

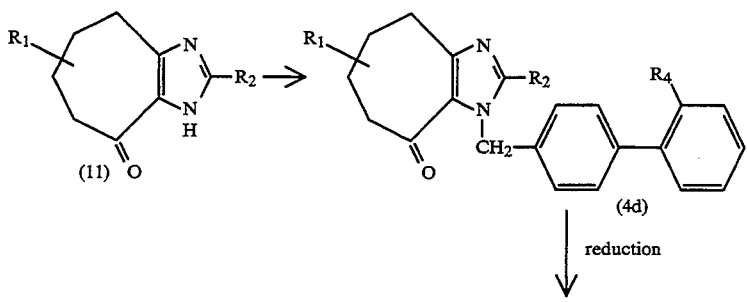

(4d)

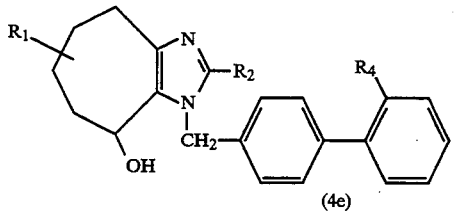

(4e)

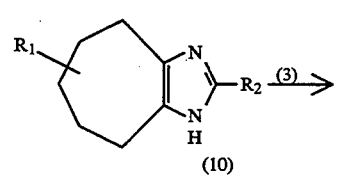

(10)

(wherein $R_1$, $R_2$ and $R_4$ are the same as mentioned above.)

The compound (4d) is obtained by the reaction of tetrahydroimidazole (11), prepared from reduction of ketoimidazole (7) with halogenomethylbiphenyl (3) or compound (4d) is obtained by reduction of the compound (4a),. The compound (4d) is reduced to obtain hydroxy compound (4e) using a reducing agent such as sodium borohydride.

Preparation of the compound in general formula (1) from the compound (4) is as follows.

a) R₄ is COOR₅ (R₅ = a lower alkyl group)
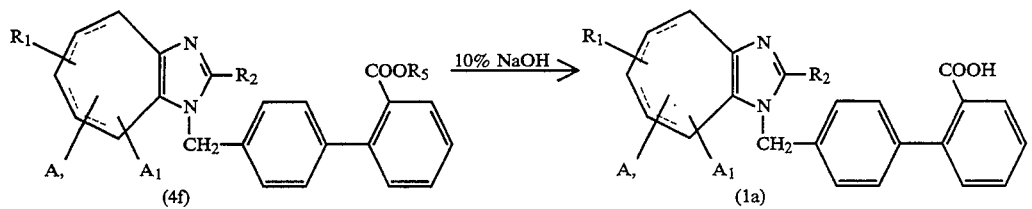
b) R₄ is CN
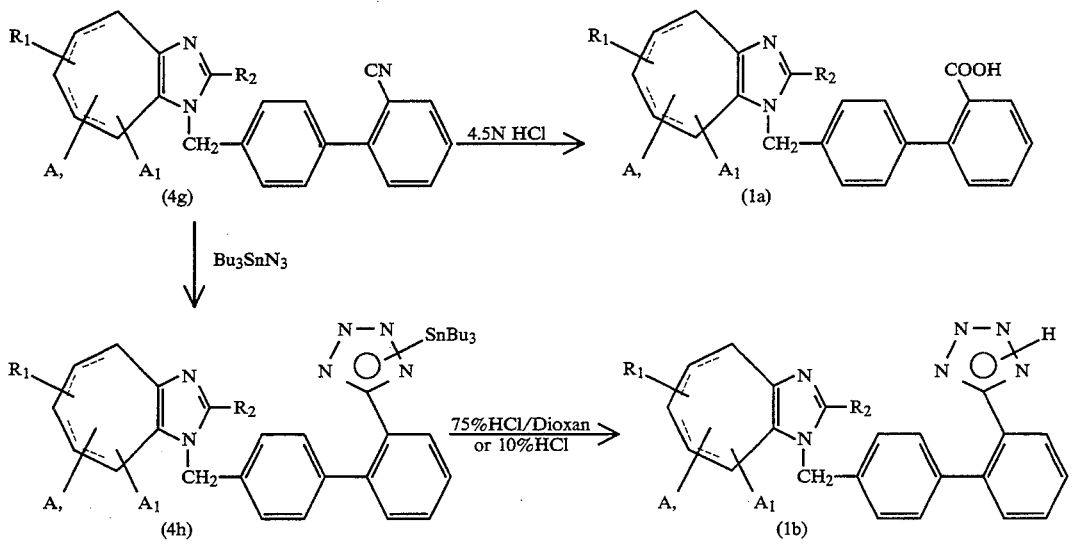
c) R₄ is ![structure]
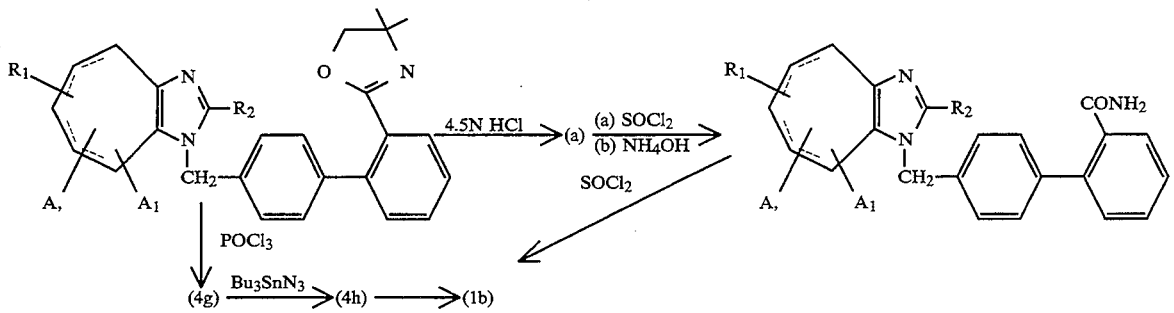
d) R₄ is ![structure]
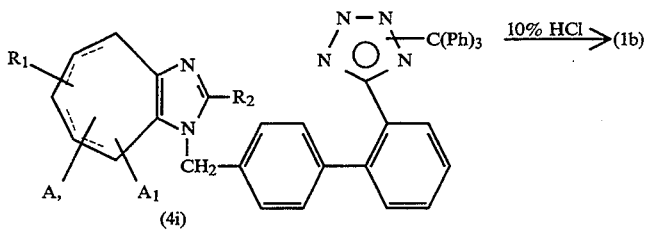

(wherein $R_1$, $R_2$, A and $A_1$ are the same as mentioned above.)

Halogenomethylbiphenyl compound (3), being the starting material, is prepared as follows.

In case of $R_4$ is oxazoline in the compound 3, this compound is prepared according to the method of A. I. Meyer et al (J. Am. Chem. Soc., 97, 7383, (1975)).

Oxazoline compound (12) is subjected to grignard reaction to obtain biphenyl compound (13), followed by halogenation to obtain halogenomethyl biphenyl compound (3c).

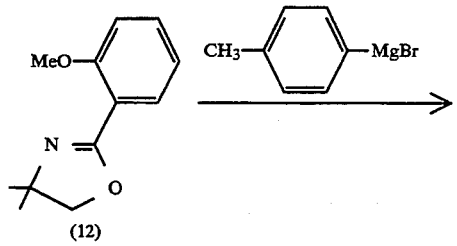

(12)

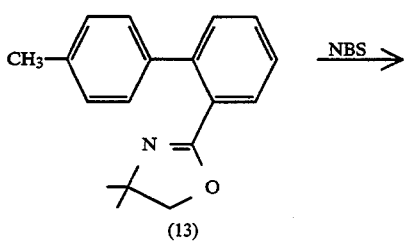

(13)

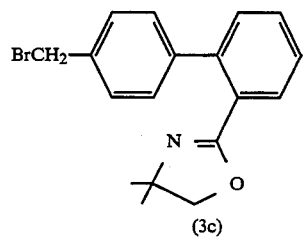

(3c)

In this step, the compound (12) is obtained from acid chloride (14) according to the method of A. I. Meyer et al. (J. Org. Chem., 39, 2787, (1974)).

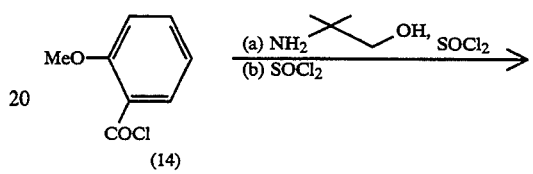

(14)

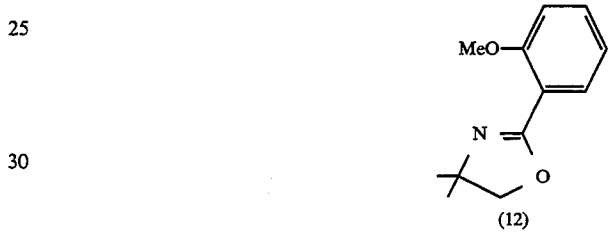

(12)

In other case of $R_4$ being $COOR_5$ ($R_5$ is a lower alkyl), CN or trityl-protected tetrazole in compound (3), these compounds are prepared as follows.

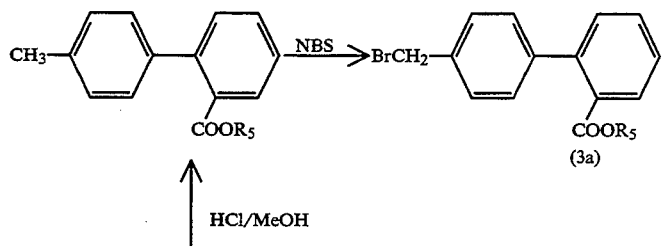

(3a)

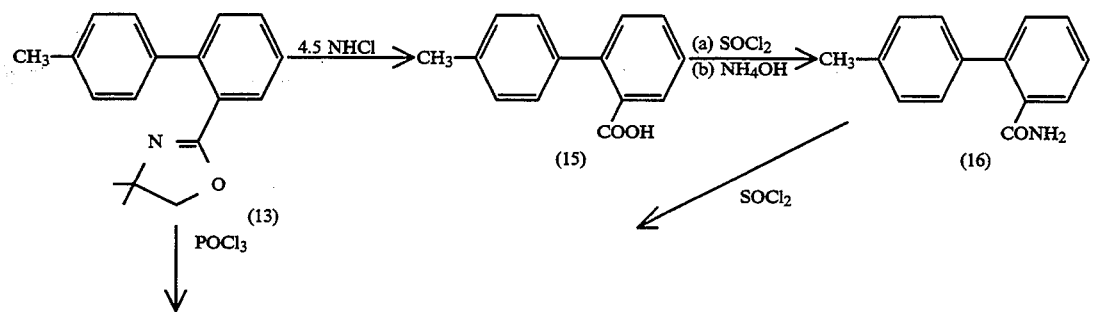

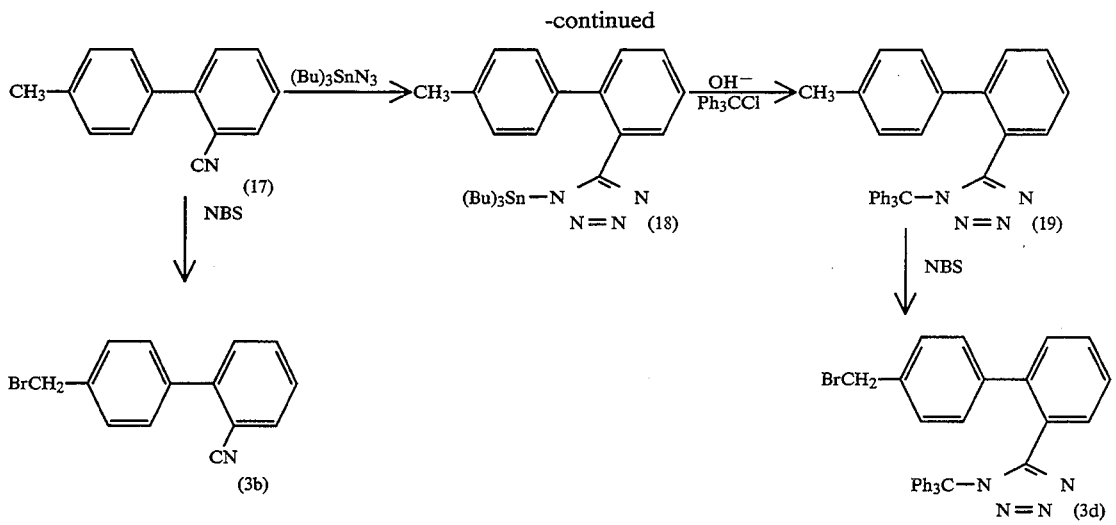

Methyl biphenyl compound (13) is hydrolyzed to obtain carboxylic acid compound (15), then this compound is esterified, halogenated to halogenomethyl compound (3a). And carboxylic acid compound (15) is converted to amide (16), then this compound is dehydroxylated to nitrile (17), halogenated to halogenomethyl compound (3b).

Nitrile (17) is refluxed with tributyltin azide (Bn3SnN3) in toluene to obtain tributyltin tetrazole (18), followed by tritylation with trityl chloride and sodium hydroxide to obtain trityl tetrazole (19). Then this compound is halogenated to halogenomethyl biphenyl compound (3d).

And also nitrile (17) is obtainable directly from biphenyl compound (13) and POCl3 according to the method of I. M. Dordor et al (Tetra. Let., 24, 1437 (1983)) without via amide (16). Furthermore tetrazole (19) is obtained by the reaction of nitrile (17) and sodium azide (NaN3) (Comprehensive Heterocyclic Chemistry. Vol. 5, 828 (1984), Ed. by Katritzky A. R., Pergamon Press).

The compounds (1) of the invention have an angiotensin II receptor antagonistic effect which will be explained later. They can be administered orally in the form of tablets, capsules, granules and syrups and also can be administered not orally such as direct administration to rectal and in the form of injections.

An effective dosage of the compound is from 10 to 100 mg once to several times a day for adults, though it may be adjusted depending on age and symptoms.

PHARMACOLOGICAL EXPERIMENT

Angiotensin II receptor antagonistic activity experiments are carded out according to P. C. Wong et al. (Hypertension. 15, 823 (1990)).

Rabbit aorta thoracic is isolated, contracted by angiotensin II. The inhibition of contraction by the compound (1) is expressed as $pA_2$ from dose-response curve (Schild, Brit. J. Pharmacol. 14, 48 (1959)).

| Compd. NO | pA2 | Compd. NO | pA2 |
|---|---|---|---|
| 1 | 7.95 | 18 | 9.3 |
| 2 | 8.7 | 18 - K salt | 9.50 |
| 3 | 9.48 | 19 | 9.4 |
| 4 | 9.3 | 20 | 7.2 |
| 9 | 8.12 | 24 | 8.75 |
| 11 | 7.7 | 25 | 9.07 |
| 15 | 8.3 | 26 | 8.01 |
| 16 | 9.0 | 27 | 7.2 |
| 17 | 9.9 | | |

Acute Toxicity Study

The acute toxicity of the compounds of this invention has been studied in rats and monkeys, according to Japanese "Guidelines for Toxicity Studies Required for Application for Approval to Manufacture (Import) Drugs".

Methods: An appropriate number of dose levels of aqueous drug solutions are orally administered to 5 male and 5 female rats (CD - BR) and 2 male and 2 female monkeys (Cynomolgus) for compound 17, and 5 male rats (CD - BR) for compounds 3, 18 and 25. The lethal doses are estimated on the basis of mortality at different dose levels in an observation period of 14 days.

Result: $LD_{50}$'s of the tested compounds are over than 3200 mg/kg.

EXAMPLE

Example 1: 5-[2-(4-(2-methyl-8-oxo-1-cycloheptimidazolyl)methylbiphenylyl)]tetrazole (Compound 1)

(a) 2-methyl-8-oxo-1-cycloheptimidazole

To a solution of sodium hydroxide (1.0 g) in water (2 mL), 1, 4-dioxane (30 mL) and methylamidine hydrochloride (1.0 g) were added and followed by addition of tosyltropolone (2.7 g) dropwise. The separated reaction mixture was stirred at room temperature for 6 hrs and poured into ice-water. The aqueous solution was treated with 10% HCl dropwise to adjust the pH 5.0. The resulting precipitate was collected by filtration, and was recrystallized with ethyl acetate. The product was obtained as a pale yellow crystal (0.5 g):
mp (°C.) 197.5-198; IR (KBr, cm$^{-1}$) 3100, 1625, 1572, 1530, 1300, 800; $^1$H-NMR (CDCl3, ppm) δ2.75 (3H, s, CH3), 6.90~7.95 (4H, m, aromatic).

(b) 1-trityl-5-[2-(4-(2-methyl-8-oxo-1(8H)-cycloheptimidazolyl) methylbiphenylyl)]tetrazole 2-methyl-8-oxo-1-cycloheptimidazole (0.5 g) was added into toluene (20 mL). 50% NaOH aqueous solution (1.5 mL) was added and the mixture was stirred at room temperature for 30 min. 1-trityl-5-(2-(4-bromomethylbiphenylyl)) tetrazole (1.91 g) and tetrabutyl-ammonium hydrogensulfate (53 mg) were then added and the reaction mixture was stirred at 40° C. for 24 hrs. The solution was filtered, and the filtrate was extracted with ethyl acetate, and the ethyl acetate layer were dried (MgSO$_4$), filtered, and concentrated in vacuo. The resulting oil was purified by column chromatography on 80 g of silica gel and eluted with n-hexane-ethyl acetate (1:1). The product was obtained as a pale yellow oil (0.4 g): IR (KBr, cm$^{-1}$) 3424, 2974, 1734, 1578, 1470, 1240, 747; $^1$H-NMR (CDCl$_3$, ppm) δ2.34 (3H, s, CH$_3$), 5.9 (2H, s, CH$_2$), 6.75~7.97 (27H, m, aromatic).

(c) 5-[2-(4-(2-methyl-8-oxo-1(H)-cycloheptimidazolyl)methylbiphenylyl)]tetrazole 1-trityl-5-[2-(4-(2-methyl-8-oxo-1(H)-cycloheptimidazolyl)methylbiphenylyl)]tetrazole (0.08 g) was dissolved in THF (2 mL). 10% HCl aqueous solution (1 mL) was added and the mixture was stirred at room temperature for 4 hrs. The mixture was treated with 10% NaOH to adjust the pH 3-3.5 and then extracted with ethyl acetate. The organic layer was dried (MgSO$_4$), filtered, and concentrated in vacuo. The resulting oil was purified by column chromatography on 10 g of silica gel, and eluted with chloroform/methanol (30/1). Compound 1 was obtained as a pale yellow crystal (30 mg): mp (°C.) 138-141; MS (m/e) 391 (M+−1), 178 (BP); IR (KBr, cm$^{-1}$) 3412, 3004, 1575, 1476, 909; $^1$H-NMR (CDCl$_3$, ppm) δ2.31 (3H, s, −CH3), 5.74 (2H, s, −CH$_2$−), 6.65-7.85 (12H, m, aromatic).

Example 2-10: (Compound 2-10)

According to the procedure described in example 1, each of compound 2-10 was prepared using starting materials corresponding to the target compounds. The formula and the melting points of compounds 2-10 are as follows:

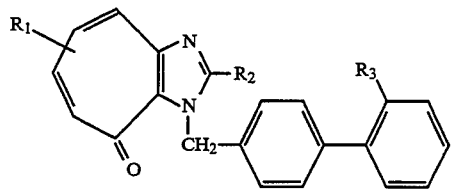

| Compound | R$_1$ | R$_2$ | R$_3$ | mp (°C.) |
|---|---|---|---|---|
| 2 | H | C$_2$H$_5$ | tetrazole | 115-8 |
| 3 | H | C$_3$H$_7$ | tetrazole | 116-8 |
| 4 | H | C$_4$H$_9$ | tetrazole | 95-6 |
| 5 | H | C$_5$H$_{11}$ | tetrazole | 97.5-99 |
| 6 | H | C$_4$H$_9$ | −COOH | 215-7 |
| 7 | 5-i-Pro | C$_4$H$_9$ | tetrazole | 116-8 |
| 8 | 6-i-Pro | C$_4$H$_9$ | tetrazole | 116-8 |
| 9 | H | i-C$_3$H$_7$ | tetrazole | 126-8 |
| 10 | H | i-C$_4$H$_9$ | tetrazole | 98-102 |

Example 11: 5-[2-(4-(2-butyl-1, 4, 5, 6, 7, 8-hexahydro-1-cycloheptimidazolyl) methylbiphenylyl)]tetrazole (Compound 11)

(a) 2-butyl-cycloheptimidazolyl

Sodium metal (0,186 g) was dissolved in absolute ethanol (20 mL) and butylamidine hydrochloride (1.2 g) was added to this solution with stirring at 0° C. Methyltropolone (1.0 g) dissolved in absolute ethanol (1.5 mL) was added and the reaction mixture was refluxed for 4 hrs. This mixture was filtered at room temperature, and the filtrate was concentrated in vacuo. The concentrate was dissolved in ethyl acetate and washed with brine followed by purification by column chromatography using silica gel and eluted with ethyl acetate/methanol (20/1). The object compound was obtained as a yellow oil: MS (m/e) 186 (M+), 144 (BP).

(b) 2-butyl-1, 4, 5, 6, 7, 8-hexahydro-1-cycloheptimidazole 2-butyl-cycloheptimidazole (0.30 g) was dissolved in methanol (50 mL). PtO$_2$ (40 mg) as catalysts was added and catalytic reduction (hydrogenation) was carried out. The reaction mixture was filtered, and the filtrate was concentrated in vacuo. The residue was purified by silica gel column chromatography in the usual way, and eluted with ethyl acetate/methanol (20/1). The object compound was obtained as a white crystal: mp (°C.) 85-87; MS (m/e) 192 (M+), 82 (BP); $^1$H-NMR (CDCl$_3$, ppm) δ0.85-1.03 (3H, t, −CH$_2$−CH$_3$), 1.19-1.91 (8H, m, Cyclo (CH$_2$)$_2$+−CH$_2$−(CH$_2$)$_2$−CH$_3$), 2.55-2.71 (6H, m, −(CH$_2$)$_3$−), 8.6 (1H, s, NH).

(c) 1-trityl-5-[2-(4-(2-butyl-1, 4, 5, 6, 7, 8)-hexahydro-1-cycloheptimidazolyl) methylbiphenylyl)]tetrazole A solution 2-butyl-1, 4, 5, 6, 7, 8-hexahydro-1-cycloheptimidazole (0.10 g) in DMF (5 mL) was made alkaline by addition of NaOH (23 mg) while cooling to about 0° C., and the mixture was stirred for 30 min. 1-trityl-5-(2-(4-bromomethylbiphenylyl)) tetrazole (0.435 g) was added and the reaction mixture was allowed to stand overnight. After addition of ethyl acetate, the mixture was washed with brine, dried ($Na_2SO_4$), filtered, and organic solvent was evaporated in vacuo. The resulting oil was purified by silica gel column chromatography eluting with ethyl acetate to yield pure object compound as a colorless oil (0.65 g): IR ($cm^{-1}$) 3004, 2926, 2854, 1722, 1638, 1446, 1215, 747, 696, 435; H-NMR ($CDCl_3$, ppm) δ0.78-0.94 (3H, t, —$CH_2CH_3$), 1.05-1.08 (8H, m, $(CH_2)_3$—$CH_3$+Cyclo—4H), 2.2-2.9 (8H, m, Cyclo $(CH_2)\times 4$), 4.88 (2H, s, $C_6H_5CH_2$), 6.41-7.52 (23H, m, aromatic).

(d) 5-[2-(4-(2-butyl-1, 4, 5, 6, 7, 8)-hexahydro-1-cycloheptimidazolyl) methylbiphenylyl)]tetrazole 1-trityl-5-[2-(4-(2-butyl-1, 4, 5, 6, 7, 8)-hexahydro-1-cycloheptimidazolyl) methylbiphenylyl)]tetrazole (0.60 g) was dissolved 1,4-dioxane (2 mL) followed by addition of 75% acetic acid (15 mL), and the reaction mixture was allowed to stand at room temperature overnight. The reaction mixture was concentrated in vacuo. The resulting product was purified by silica gel column chromatography in a usually way. After election with chloroform/methanol (10/1), the object compound was obtained as a white crystal (0.35 g): MS (m/e) 426 ($M^+$), 149 (BP); H-NMR ($CDCl_3$, ppm) δ0.80 (3H, t, —$CH_2CH_3$), 0.92-1.78 (10H, m, $CycloCH_2\times 2$+$(CH_2)_3$—$CH_3$), 2.3-2.7 (8H, m, $CycloCH_2\times 3$+$CH_2$), 5.09 (2H, s, $CH_2$—$C_6H_5$—), 6.68-6.78 (2H, d, aromatic), 6.55-7.20 (4H, dd, aromatic), 7.23-7.59 (4H, m, aromatic).

Example 12-14: (Compound 12-14)

2-acetyl-4-isopropyltolopolone or 2-acetyl-5-isopropyltolopolone was reduced according to the procedure of catalytic reduction mentioned in (b) of example 11. The resulting 2-acetyl-4 or 5-isopropyl-2, 3, 4, 5, 6, 7-hexahydrotolopolone was converted to 2-alkyl-1, 4, 5, 6, 7, 8-hexahydro-1-cycloheptimidazoles according to the procedure mentioned in (a) of example 11. Then, these cycloheptimidazoles was led to the final products as shown in Table 3 according to the procedure mentioned in (b) and (c) of example 1. In case of 2-acetyl-5-isopropyltolopolone as a starting material, the regioisomers of compound 13 and compound 14 (51.0 and 45.2%, respectively) were obtained.

TABLE 3

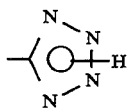

| Compound | $R_1$ | $R_2$ | $R_3$ | mp (°C.) |
|---|---|---|---|---|
| 12 | 6-i-Pro | $C_4H_9$ | tetrazole | 63-4 |
| 13 | 5-i-Pro | $C_4H_9$ | tetrazole | 61-2 |
| 14 | 7-i-Pro | $C_4H_9$ | tetrazole | 78-9 |

Example 15: 5-[2-(4-(2-methyl-8-oxo-5, 6, 7, 8-tetrahydro-1(4H)-cycloheptimidazolyl) methylbiphenyl)]tetrazole (Compound 15)

(a) 1-trityl-5-[2-(4-(2-methyl-8-oxo-5, 6, 7, 8-tetrahydro-1(4H)-cycloheptimidazolyl) methylbiphenylyl)]tetrazole After replacing the air in the vessel by a stream of argon, a solution of 1-trityl-5-[2-(4-(2-methyl-8-oxo-1-cycloheptimidazolyl)methylbiphenylyl)]tetrazole (0.4 g) prepared by method (b) of example 1 in THF (4 mL) was hydrogenated over $PrO_2$ (38 mg) at room temperature. The reaction mixture was filtered, and filterate was concentrated in vacuo. The resulting product was purified by silica gel column chromatography in a usually way. Elution was carried out with n-hexane/ethyl acetate (1/3): H-NMR ($CDCl_3$, ppm) δ1.68-1.98, 2.05-3.05 (8H, m, Cyclohepta ring), 2.19 (3H, s, —$CH_3$), 5.44 (2H, s, —$CH_2$—), δ6.67-7.95 (23H, m, aromatic).

(b) 5-[2-(4-(2-methyl-8-oxo-5, 6, 7, 8-tetrahydro-1(4H)-cycloheptimidazolyl) methylbiphenylyl)]tetrazole:

A mixture of 1-trityl-5-[2-(4-(2-methyl-8-oxo-5, 6, 7, 8-tetrahydro-1 (4H)-cycloheptimidazolyl)methylbiphenylyl)]tetrazole (0.35 g) and 10% HCl (13.5 mL) in THF (7 mL) was stirred at room temperature for 3 hrs. The mixture was adjusted pH 3-3.5 with 10% NaOH and extracted with ethyl acetate. Ethyl acetate layer was concentrated. The resulting product was purified by silica gel column chromatography in a usually way. Elution was effected with chloroform/methanol (30/1). The object compound was obtained as a whim crystal (0.175 g): mp (°C.) 142-143.5; MS (m/e) 398 ($M^+$), 178 (BP); IR ($cm^{-1}$, KBr) 2920, 1638, 1479, 1422, 1392, 753; H-NMR ($CDCl_3$, ppm) δ1.55-1.90, 2.30-2.70 (8H, m, Cyclohepta ring), 2.06 (3H, s, $CH_3$), 5.44 (2H, s, —$CH_2$—), 6.65-7.04, 7.28-7.86 (8H, m, aromatic).

Example 16-25: (Compound 16-25)

Compounds 16-25 as shown in Table 4 were prepared in a similar manner as described in Example 15.

TABLE 4

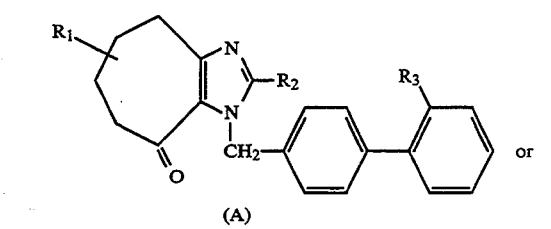

(A)

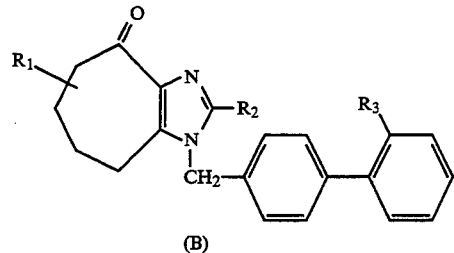

(B)

or

| Compound | R₁ | R₂ | R₃ | | mp (°C.) |
|---|---|---|---|---|---|
| 16 | A | H | C₂H₅ | 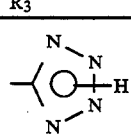 | 124–6 |
| 17 | A | H | C₃H₇ | 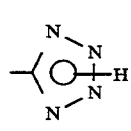 | 134–6 |
| 18 | A | H | C₄H₉ | 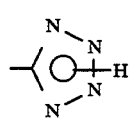 | 109–110.5 |
| 19 | A | H | C₅H₁₁ | 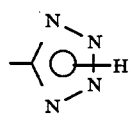 | 103–104 |
| 20 | B | H | C₄H₉ | 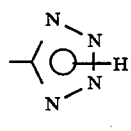 | 118–120 |
| 21 | A | 5-i-Pro | C₄H₉ | 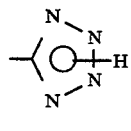 | 87–9 |
| 22 | A | 6-i-Pro | C₄H₉ | 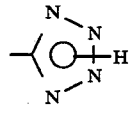 | 83–5 |
| 23 | A | H | C₄H₉ | COOH | 210° decomposition |
| 24 | A | H | i-C₃H₇ | 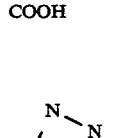 | 108–110 |

TABLE 4-continued

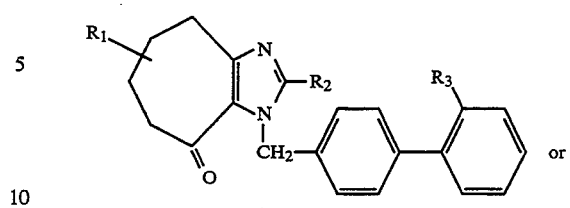

(A)

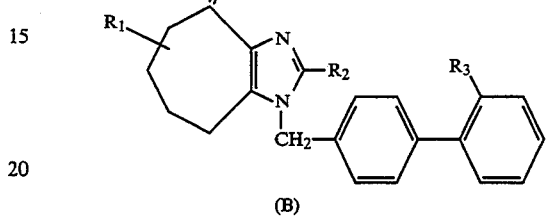

(B)

or

| Compound | R₁ | R₂ | R₃ | | mp (°C.) |
|---|---|---|---|---|---|
| 25 | A | H | i-C₄H₉ | 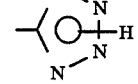 | 110–113 |

In case of the preparation of compound 20, 2-butyl-8-oxo-1-cycloheptimidazole was reduced by the method as described in the step (a) of Example 13 to yield compound as shown in formula (26). The resulting compound was reacted with 1-trityl-5(2-(4-bromomethylbiphenylyl)]tetrazole in the presence of NaH in DMF. Compound 18 (14.6%) and its regioisomer, compound 20 (60.0%), were obtained.

Example 26 and 27: (Compound 26 and 27)

1-trityl-5-[2-(4-(2-butyl-8-oxo-5, 6, 7, 8-tetrahydro-1(4H)-cycloheptimidazolyl) methylbiphenylyl)]tetrazole and 1-trityl-5-[2-(4-(2-butyl-4-oxo-4, 5, 6, 7- tetrahydro-1 (8H)-cycloheptimidazolyl)methylbiphenylyl)]tetrazole obtained as the intermediates from the process of compound 18 and 19, respectively, were reduced at 0° C. for 2 hrs in THF in a usual manner using LiAlH₄ as a reductant. Each of the resulting compounds was detritylized by the procedure described in (b) of example 15 to yield compound 26 and 27, respectively, as shown in Table 5.

TABLE 5

| Compound | | mp (°C.) |
|---|---|---|
| 26 | | 112.5–3 |

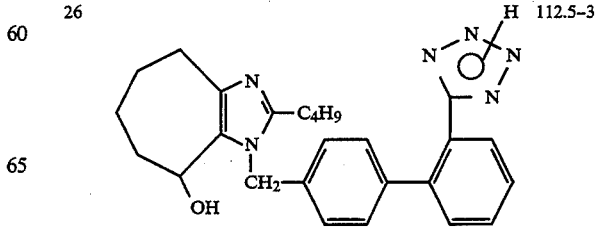

TABLE 5-continued

| Compound | | mp (°C.) |
|---|---|---|
| 27 | 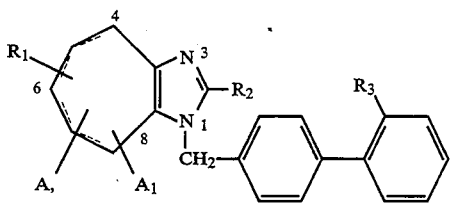 | H 121-3 |

We claim:

1. A compound of the formula (1) or a salt thereof,

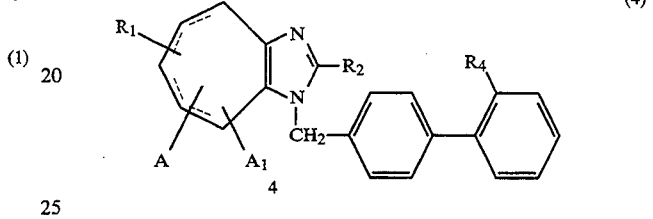

(1)

wherein $R_1$ represents hydrogen or isopropyl;
$R_2$ represents lower alkyl;
$R_3$ represents a carboxyl or tetrazolyl;
A and $A_1$ are each, individually, substituents at the 4- or 8-position,
A represents hydrogen, and
$A_1$ represents hydrogen or hydroxy, or
A and $A_1$ together form an oxo group at the 4- or 8-position; and the lines "═══" represent two double bonds or a saturated single bond.

2. The compound of claim 1 wherein A and $A_1$ form an oxo group.

3. The compound of claim 2 wherein the oxo group is at the 4-position.

4. The compound of claim 2 wherein the oxo group is at the 8-position.

5. The compound of claim 1 wherein A represents hydrogen.

6. The compound of claim 5 wherein $A_1$ represents hydrogen.

7. The compound of claim 5 wherein $A_1$ represents hydroxyl.

8. The compound of claim 7 wherein the hydroxyl is at the 4-position.

9. The compound of claim 7 wherein the hydroxyl is at the 8-position.

10. The compound of claim 1 wherein

represents a single bond.

11. The compound of claim 1 wherein

represents two double bonds.

12. The compound of claim 1 wherein $R_1$ represents isopropyl.

13. The compound of claim 1 wherein $R_1$ represents hydrogen.

14. The compound of claim 1 wherein $R_3$ represents carboxyl.

15. The compound of claim 1 wherein $R_3$ represents tetrazolyl.

16. A compound of formula (4)

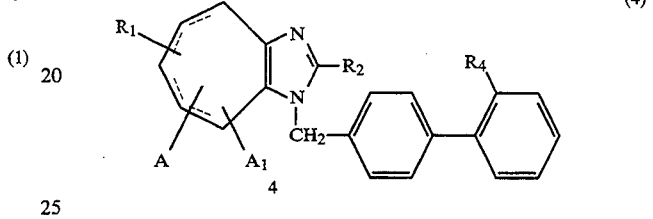

(4)

wherein $R_1$ represents hydrogen or isopropyl;
$R_2$ represents a lower alkyl;
A and $A_1$ are each, individually, substituents at the 4- or 8-position;
A represents hydrogen, and
$A_1$ represents hydrogen or hydroxy, or
A and $A_1$ together represents an oxo group at the 4- or 8-position; the lines ═══ represent two double bonds or a saturated single bond; and
$R_4$ represents $COOR_5$, CN,

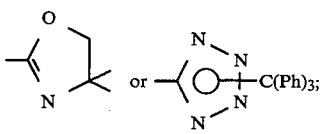

wherein $R_5$ represents lower alkyl, and Ph represents phenyl.

17. A pharmaceutical composition comprising, as active ingredient, a compound of formula (1) as set forth in claim 1 or a salt thereof with a pharmaceutically acceptable base, and a pharmaceutically acceptable carrier.

18. A method for treating hypertension in a patient in need thereof comprising administering to such patient a pharmacologically effective amount of the compound of formula (1) as set forth in claim 1 or a pharmaceutically acceptable salt thereof.

19. A method for treating congestive heart failure in a patient suffering therefrom comprising administering to such patient a pharmacologically effective amount of the compound of formula (1) as set forth in claim 1 or a pharmaceutically acceptable salt thereof.

20. A method for lowering intraocular pressure in a patient in need thereof comprising administering to such patient a pharmacologically effective amount of the compound of formula (1) as set forth in claim 7 or a pharmaceutically acceptable salt thereof.

* * * * *